US007666913B2

(12) United States Patent
Kadota et al.

(10) Patent No.: US 7,666,913 B2
(45) Date of Patent: Feb. 23, 2010

(54) METHOD OF TREATING OR PREVENTING OSTEOPOROSIS USING ISOTAXIRESINOL DERIVED FROM TAXUS YUNNANENSIS

(75) Inventors: Shigetoshi Kadota, Toyama (JP); Takahiro Nobukawa, Sagamihara (JP)

(73) Assignee: Kotosugi Inc., Sagamihara-shi (JP)

( * ) Notice: Subject to any disclaimer, the term of this patent is extended or adjusted under 35 U.S.C. 154(b) by 740 days.

(21) Appl. No.: 10/570,252

(22) PCT Filed: Jan. 27, 2005

(86) PCT No.: PCT/JP2005/001055
§ 371 (c)(1),
(2), (4) Date: Mar. 2, 2006

(87) PCT Pub. No.: WO2005/074905
PCT Pub. Date: Aug. 18, 2005

(65) Prior Publication Data
US 2009/0143483 A1 Jun. 4, 2009

(30) Foreign Application Priority Data
Feb. 3, 2004 (JP) ............................. 2004-026535

(51) Int. Cl.
A61K 31/05 (2006.01)
A61P 19/10 (2006.01)
(52) U.S. Cl. ................. 514/729; 424/195.15
(58) Field of Classification Search .................. None
See application file for complete search history.

(56) References Cited

U.S. PATENT DOCUMENTS

| | | | |
|---|---|---|---|
| 6,261,565 B1 | 7/2001 | Empie et al. | |
| 6,335,038 B1 | 1/2002 | Cavazza | |
| 6,417,224 B1 | 7/2002 | Ohta et al. | |
| 2001/0016590 A1 | 8/2001 | Ahotupa et al. | |
| 2002/0165169 A1 | 11/2002 | Kim et al. | |
| 2003/0144216 A1 | 7/2003 | Unkila | |
| 2005/0158435 A1 | 7/2005 | Abe et al. | |
| 2006/0035964 A1 | 2/2006 | Kadota et al. | |

FOREIGN PATENT DOCUMENTS

| | | |
|---|---|---|
| JP | 9-12592 | 1/1997 |
| JP | H11-221048 A | 8/1999 |
| JP | 2002-518437 A | 6/2002 |
| JP | 2003-63971 | 3/2003 |
| JP | 2004-507499 A | 3/2004 |
| WO | 99/44621 A1 | 9/1999 |
| WO | 2002/017909 A1 | 3/2002 |
| WO | 2003/075686 A1 | 9/2003 |
| WO | 2004-009065 A1 | 1/2004 |

OTHER PUBLICATIONS

Guo et al. (AN: 1994:692369, abstract, Chinese Pharmaceutical Jouranl, 1994, 46(3), 175-83).*
Liu et al. (AN 1985:565998, abstract, Taiwan Kexue, 1984, 38(3), 119-25).*
Niina M. Saarinen et al.; Uptake and Metabolism of Hydroxymatairesinol in Relation to Its Anticarcinogenicity in DMBA-Induced Rat Mammary Carcinoma Model; Nutrition and Cancer, vol. 41, Nos. 1 & 2, 2001, pp. 82-90. Cited in the ISR.
F. E. King et al.; iso-Taxiresinol* (3'-Demethylisolariciresinol), a New Lignan extracted from the Heartwood of the English Yew, *Taxus baccata*, J. Chem. Soc., 1952, pp. 17-24. Cited in the spec.
International Search Report dated Mar. 15, 2005 of PCT/JP2005/001055.
Notification of Reason(s) for Refusal, dated Oct. 2, 2009, in corresponding Japanese Application No. 2005-517653.

* cited by examiner

*Primary Examiner*—Brian-Young S Kwon
(74) *Attorney, Agent, or Firm*—Westerman, Hattori, Daniels & Adrian, LLP

(57) ABSTRACT

The object of the present invention is to provide a drug effective in treating or preventing osteoporosis. The present invention discloses a therapeutic or preventive drug for osteoporosis having a compound shown in the formula (1)

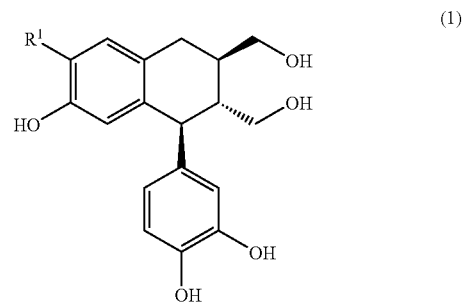

(1)

(wherein $R^1$ is an alkyloxy group with the carbon number of 1 to 4) or a pharmaceutically acceptable salt or ester of said compound in the formula (1) as an effective ingredient. In the compound of the formula (1), a substance in which $R^1$ is $CH_3O$ is isotaxiresinol derived from *Taxus yunanennsis* and showed physiological activities in inhibiting bone resorption and improving bone formation.

6 Claims, No Drawings

METHOD OF TREATING OR PREVENTING OSTEOPOROSIS USING ISOTAXIRESINOL DERIVED FROM TAXUS YUNNANENSIS

TECHNICAL FIELD

The present invention relates to a therapeutic or preventive drug for osteoporosis comprising isotaxiresinol and analogous compounds as effective ingredient.

BACKGROUND ART

Lignan compounds derived from *Taiwania flousiana* are known for its effective inhibition of bone resorption (refer to a patent document 1 for instance). Further, pinoresinol derived from *Forsythia suspense* Vahl is known for its effective palliation of symptoms of menopausal discomfort. It is suggested that pinoresinol is effective in preventing osteoporosis (refer to a patent document 2 for instance).

Patent document 1: Japanese Patent Laid-Open H09-12592 bulletin

Patent document 2: Japanese Patent Laid-Open 2003-63971 bulletin

DISCLOSURE OF THE INVENTION

Object of the Invention

The object of the present invention is to provide a drug effective in treating or preventing osteoporosis.

Method to Achieve the Object

The present inventors have found that isotaxiresinol derived from *Taxus yunnanensis* shows physiological activities in inhibiting bone resorption and improving bone formation in vivo and have completed the present invention.

Namely, the present invention is a therapeutic or preventive drug for osteoporosis comprising a compound shown in the formula (1)

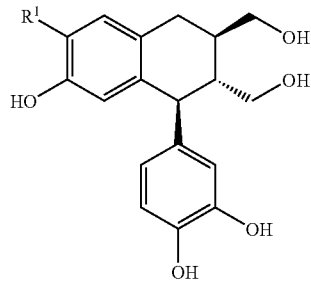

(1)

(wherein $R^1$ is an alkyloxy group with the carbon number of 1 to 4)
or a pharmaceutically acceptable salt or ester of said compound in the formula (1) as an effective ingredient.

EFFECTIVENESS OF THE INVENTION

A drug of the present invention not only inhibits bone resorption, but also improves bone formation, and therefore is effective in treating and preventing osteoporosis.

MOST PEFERRED EMBODMENT TO CARRY OUT THE INVENTION

In the present invention, ester means a compound in which a hydroxyl group of a methylol group ($CH_2OH$) and/or a phenolic hydroxyl group in the formula (1) bind with an organic acid or an inorganic acid, and a water molecule is removed. Any of the pharmaceutically acceptable esters commonly known in the medical and pharmaceutical fields may be used without restriction. For example, acetic acid may be used as an organic acid, and phosphoric acid may be used as an inorganic acid.

Any of the salts derived from an inorganic or organic base is acceptable, including a salt in which a methylol group in a compound becomes a methyloxide ion group and/or a salt in which a phenolic hydroxyl group becomes a phenoxide ion group. Any of the pharmaceutically acceptable salts commonly known in the medical and pharmaceutical fields may be used without restriction. For example, alkaline metal, alkaline earth metal, and amine salts may be used.

In the compound of the formula (1), when $R^1$ is $CH_3O$, a compound of the resulting formula, i.e., the formula (2),

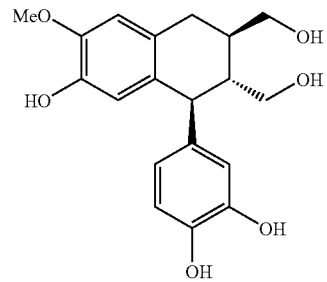

(2)

is isotaxiresionl (hereinafter called "ITX").

ITX, which is contained in the wood (leaves, bark, body, core, roots and the like) of *Taxus yunnanensis*, can be extracted and isolated in the following steps. First, the wood was extracted with heated water to obtain an aqueous extract. Second, the aqueous extract was extracted with an organic solvent (e.g., ethyl acetate) to obtain an organic solvent fraction. Third, these compounds are isolated from the organic solvent fraction by means of chromatography (column chromatography, thin-layer chromatography, HPLC and the like).

A methoxy group of ITX may be substituted by an ethoxy group, a propyloxy group or a butyloxy group. Compounds in the formula (1) can be organically synthesized from ITX.

Drugs of the present invention may be administered orally, parenterally or subcutaneously. Any administration method commonly used for drugs, such as tablet, coated tablet, capsule, solution, syrup, powder and suppository, may be used without restriction.

Tablets may be manufactured by mixing a compound(s) or an extract(s) with a vehicle (lactose, glucose, sucrose, mannitol and the like), a disintegrating agent (cornstarch, alginic acid and the like), a binder (starch, gelatin and the like), a lubricant (magnesium stearate, talc and the like) and/or delayed-release agents (carboxymethyl cellulose, cellulose acetate phthalate, polyvinyl alcohol and the like). Tablets with one or more layers are acceptable.

Coated tablets may be manufactured by coating a core manufactured in the same way as tablets are done with materials commonly used for tablet coating, such as collidone, shellac, gum Arabic, talc, titanium dioxide, and sucrose. Coated tablets with one or more layers are acceptable for delayed-release. The vehicles described above may be used.

Solutions and syrups can be fabricated by appropriately adding water, saccarides (erythritol, xylitol, mannitol, sucrose, trehalose, maltose, fructose, sorbit, honey and the like), antiseptic agents (paraben and the like), aroma chemicals, coloring agents, and oils (soybean oil and the like) to a compound(s) of the formula (1).

Capsules containing a drug of the present invention may be manufactured by encapsulating a compound(s) or an extract(s) with a gelatin capsule or by mixing a compound(s)

or an extract(s) with an inactive support(s) such as lactose and sorbitol and then encapsulating the mixture with a gelatin capsule or wrapping it with a gelatin film.

A dose of a compound(s) of the formula (1) is commonly 1 to 1,000 mg/person/day. However, an appropriate dose is intended to be decided by first administering a small amount of the compound(s) and then increasing the dose until the intended effect is obtained.

A compound(s) of the formula (1) is a compound(s) of *Taxus yunnanensis*, a medical plant that has been safely ingested, and is a safe substance(s).

EXAMPLE 1

The present invention is explained in more detail by the following embodiment. Materials, extraction methods of compounds and the like described in the embodiment of the present invention are merely examples and are not intended to restrict the scope of the present invention thereto.

(Isolation)

A body and bark (collectively "xylem") of *Taxus yunnanensis* was grinded by a grinder to obtain powder of 30 mesh pass. The powder was dried. The dried powder (850 g) was extracted with purified water (4 L) under reflux for 45 minutes. A residue remaining after filtration was further extracted with purified water (4 L) under reflux for 45 minutes. Furthermore, the same extraction operation was carried out once again. Aqueous solution layers obtained after the three extractions were collected and then evaporated to obtain 52.5 g of aqueous extract.

Next, the aqueous extract (52.5 g) was extracted with ethyl acetate (500 mL), and an ethyl acetate layer was separated. A residue remaining after the separation was further extracted with ethyl acetate (500 mL). Furthermore, the same extraction operation was carried out once again. Ethyl acetate layers obtained after the three extractions were collected and then evaporated to obtain 34.1 g of ethyl acetate fraction.

The ethyl acetate fraction (34.1 g) was applied on a silica gel column (inner diameter 3.5 cm, length 60 cm, packing materials: silica gel 60 (Nacalai Tesque, Inc.)) and eluted with a solvent of methanol and chloroform to obtain 9 fractions of each 500 mL. Table 1 shows the composition of the solvent, the weight of the elute obtained after the vacuum concentration of each fraction, and the components contained in each fraction.

TABLE 1

Column chromatography of ethyl acetate soluble fractions

| Fraction Number | Composition of Solvent (*1) MeOH % | Weight (g.) | Components |
|---|---|---|---|
| 1 | 0 | 0.31 | |
| 2 | 0 | 0.30 | |
| 3 | 1 | 0.30 | |
| 4 | 1-5 (*2) | 2.78 | SIL |
| 5 | 5 | 1.68 | SIL, TAX, HYL |
| 6 | 10 | 12.5 | |
| 7 | 10-20 (*3) | 7.84 | ITX |
| 8 | 20 | 1.41 | |
| 9 | 30 | 1.00 | |

(*1) The solvent is a mixture of chloroform and methanol. The figures in the line show the ratio of the methanol to the mixture in percentage.
(*2) The fraction mixed with the eluate at 1%: 100 mL, 2%: 100 mL, 3%: 100 mL, 4%: 100 mL, and 5%: 100 mL.
(*3) The fraction mixed with the eluate at 12%: 100 mL, 14%: 100 mL, 16%: 100 mL, 18%: 100 mL, and 20%: 100 mL.

The structure of ITX was identified and confirmed on the basis of spectral and chemical analyses. The major analytical data are given below:

ITX (isotaxiresinol): colorless amorphous solid $^1$H NMR (CD$_3$OD), δ 6.69 (1H, d, J=8.0 Hz, H-5'), 6.61 (1H, s, H-5), 6.52 (1H, d, J=2.0 Hz, H-2'), 6.50 (1H, dd, J=2.0, 8.0 Hz, H-6'), 6.19 (1H, s, H-2), 4.67 (2H, m, H-9), 4.67 (1H, m, H-9'), 4.66 (1H, d, J=6.9 Hz, H-7'), 3.77 (3H, s, H—OMe), 3.40 (1H, dd, J=4.3, 11.1 Hz, H-9'), 2.73 (1H, br d, J=6.8 Hz, H-7), 1.97 (1H, m, H-8), 1.71 (1H, m, H-8')

$^{13}$C NMR (CD$_3$OD) δ 147.1 (C-3), 146.2 (C-3'), 145.2 (C-4), 144.6 (C-4'), 138.7 (C-1'), 134.3 (C-1), 128.9 (C-6), 122.0 (C-6'), 117.4 (C-2), 117.3 (C-2'), 116.1 (C-5'), 112.3 (C-5), 66.0 (C-9), 62.4 (C-9'), 56.4 (C—OMe), 48.1 (C-8'), 47.8 (C-7'), 40.1 (C-8), 33.5 (C-7)

[α] $D^{25}$ +47.3° (c=0.4 in Ethanol)

The identified structure of ITX was found to be identical to that described in King, F. E.; L. Jurd & King, T. J., isoTaxiresinol (3'-Demethyl isolariciresinol), A New Lignan extracted from the Heartwood of the English Yew, *Taxus baccata*; J. Chem. Soc., 17-24 (1952).

In Table 1, SIL is Secoisolariciresinol; TAX is Taxiresinol; and HYL is (7'R)-7'-Hydroxylariciresinol.

Example—Antiosteoporotic Activity

Antiosteoporotic Activity of ITX was Assessed by Using Rats.

Each of the animal groups for experiments included comprised 10 rats. Ovaries were removed from female Wistar rats (age: 8 months, weight: 260-330 g). ITX, suspended in 1% water solution of carboxymethl cellulose sodium salt, was orally administered to rats of one group in a dose of 50 mg/kg (weight of rat) and to rats of another group in a dose of 100 mg/kg (weight of rat) 6 times per week after 2 weeks of the removal. 17β-estradiol (hereinafter abbreviated as "E2"), dissolved in a mixture of 5% benzyl alcohol and 95% corn oil, was injected into the abdominal cavity of rats of another group in a dose of 0.1 mg/kg (weight of rat) as positive control.

An OVX (ovariectomized) group was prepared as negative control. Furthermore, another group was sham-operated as a Sham group. The OVX group and the Sham group were only fed, with no compound or drug given.

Tibial characteristics of the rats, which were anesthetized in advance, were measured by means of peripheral quantitative computed tomography (pQCT) 6 weeks after the initiation of the administration (i.e., 8 weeks after the removal of the ovaries). In the measurement, the left tibiae were scanned with a pQCT system XCT Research M (manufactured by Stratec Medizintechnik GmbH, Germany). Voxel size was set to 0.08 mm, slice thickness was set to 0.5 mm, and cortical BMD threshold was set to 464 mg/cm$^3$. Furthermore, peel mode was set to 20 to divide total bone into cortical bone or cancerous bone.

A growth plate was identified after preliminary scanning (scout scan), and then a reference position was identified. Next, transverse image sets of four cross-sectional slices were scanned at a region of 1 to 5 mm under the growth plate. Cortical BMC and BMD and cancellous BMC and BMD, thickness of cortical bone, and periosteal circumference and endosteal circumference of cortical bone were measured at a separation mode of 3 and a contour mode of 2. Three indices of bone strength (X-, Y-, and Polar-axes) were also measured, and the data obtained were processed by XCT Research Series Manual Software Version 5.4, in which case the standard cortical BMD was set to 1,200 mg/cm$^3$.

Furthermore, a tibia, a femur, and a uterus were removed from every rat and then weighted.

Table 2 shows the results of the measurements of the weight and length of tibiae and femora of the rats of each group.

TABLE 2

Weight and length of tibiae and femora of the rats of each group

| Parameters | Sham | OVX | E2 | ITX 100 | ITX 50 |
|---|---|---|---|---|---|
| Tibia Weight (g) | 548 ± 94 | 565 ± 72 | 547 ± 94 | 562 ± 95 | 588 ± 52 |
| Tibia Length (cm) | 3.93 ± 0.19 | 3.94 ± 0.18 | 3.76 ± 0.14 | 3.97 ± 0.24 | 3.98 ± 0.14 |
| Femur Weight (g) | 871 ± 95 | 864 ± 76 | 861 ± 65 | 897 ± 83 | 862 ± 64 |
| Femur Length (cm) | 3.59 ± 0.16 | 3.64 ± 0.18 | 3.59 ± 0.15 | 3.59 ± 0.22 | 3.64 ± 0.05 |

In the table, ITX 100 is a group of the rats which ITX was given to in a dose of 100 mg/kg, and ITX 50 is a group of the rats which ITX was given to in a dose of 50 mg/kg. E2 is a group of the rats which E2 was given to. The figures in each column of the table show averages and standard deviations of the measured values. The presentation of the figures applies to Table 3 and Table 4 as well.

The tibia weight of the ITX50 group and the femur weight of the ITX100 group increased, compared with those of the OVX group; however, no significant difference was identified between the groups.

Table 3 shows the results of the measurements of BMC, BMD, bone strength indices, etc. of proximal tibia bone.

TABLE 3

BMC, BMD, bone strength indices, etc. of proximal tibia bone

| | Sham | OVX | E2 | ITX100 | ITX50 |
|---|---|---|---|---|---|
| Total bone | | | | | |
| BMC (mg/mm) | 10.7 ± 1.2 | 9.64 ± 0.63 | 10.5 ± 0.7* | 9.82 ± 0.37 | 10.4 ± 0.8* |
| BMD (mg/cm$^3$) | 744 ± 34 | 660 ± 39### | 723 ± 38 | 683 ± 21 | 707 ± 14* |
| Cancellous bone | | | | | |
| BMC (mg/mm) | 1.03 ± 0.23 | 0.84 ± 0.14 | 0.96 ± 0.17 | 1.04 ± 0.15* | 0.99 ± 0.12 |
| BMD (mg/cm$^3$) | 250 ± 32 | 212 ± 17## | 244 ± 53** | 207 ± 28 | 215 ± 25 |
| Cortical bone | | | | | |
| BMC (mg/mm) | 7.77 ± 0.84 | 6.90 ± 0.59# | 7.58 ± 0.48* | 7.40 ± 0.29 | 7.72 ± 0.52* |
| BMD (mg/cm$^3$) | 1132 ± 21 | 1121 ± 13 | 1143 ± 22* | 1138 ± 17* | 1137 ± 14* |
| Cortical bone thickness (mm) | 0.59 ± 0.05 | 0.51 ± 0.04## | 0.56 ± 0.03* | 0.55 ± 0.03* | 0.58 ± 0.03** |
| Peri. C. (mm) | 13.3 ± 0.4 | 13.6 ± 0.4 | 13.4 ± 0.6 | 13.6 ± 0.4 | 13.7 ± 0.5 |
| Edno. C. (mm) | 7.12 ± 0.92 | 10.5 ± 0.5## | 9.79 ± 0.57* | 9.97 ± 0.37* | 9.92 ± 0.54* |
| Bone strength index | | | | | |
| PSSI | 10.5 ± 1.5 | 8.91 ± 0.74# | 10.1 ± 1.17 | 9.34 ± 0.70 | 10.35 ± 0.89** |
| YSSI | 5.62 ± 1.13 | 5.20 ± 0.70 | 6.36 ± 1.13* | 5.71 ± 0.41 | 6.45 ± 0.67** |
| XSSI | 5.29 ± 0.59 | 4.51 ± 0.49# | 5.20 ± 0.56* | 4.77 ± 0.68 | 5.15 ± 0.62* |

Table 3 shows the data of cross-sectional measurements 1 mm under the growth plate of proximal tibia bone. The figures in the total bone columns show the values of the whole bone obtained by measuring cancellous bone and cortical bone together. BMC is bone mineral content, and BMD is bone mineral density. # marks show Student's t-test results (# $p<0.05$, ##$p<0.01$, ###$p<0.001$ significantly different from the Sham group), and asterisks (* mark) show Student's t-test results (*$p<0.05$, $p<0.01$, *$p<0.001$, significantly different from the OVX group). The presentation of t-test results applies to Table 4 as well.

The OVX group showed a significant decrease in total BMD and cancellous BMD and cortical BMC, compared to the Sham group. The comparison of the difference between the ITX100 group and the Sham group and the difference between the OVX group and the Sham group revealed that the ITX100 group showed inhibition of decrease in cancellous BMC and cortical BMD, compared to the OVX group. The comparison of the difference between the ITX50 and the Sham group and the difference between the OVX group and the Sham group revealed that the ITX50 showed inhibition of decrease in total BMD, cortical BMD and cortical BMC, compared to the OVX group. The comparison of the difference between the E2 group and the Sham group and the difference between the OVX group and the Sham group revealed that the E2 group showed inhibition of decrease in all but except total BMD and cancellous BMC, compared to the OVX group.

Compared to the Sham group, the OVX group showed an increase in periosteal circumference (Peri. C.) and endosteal circumference (Endo. C.) and a significant decrease in cortical bone thickness (13.6% less than the Sham group). These results demonstrate that the bone metabolism turnover was accelerated, leading to higher bone resorption than bone formation.

The ITX50 group and the ITX100 group showed inhibition of increase in endosteal circumference, compared to the OVX group. This indicate that bone resorption on endosteal surface was inhibited. On the other hand, the ITX50 group and the ITX100 group showed the same level or an increase in periosteal circumference, compared to the OVX group, indicating that ITX does not inhibit bone formation. Consequently, ITX inhibits a decrease in cortical bone thickness, with almost the same thickness as the Sham group (the ITX50 group: 98.3% that of the Sham group and the ITX100 group: 93.2% that of the Sham group).

Both the inhibition of increase in endosteal circumference and the inhibition of decrease in cortical bone thickness observed in the ITX50 group and ITX100 group indicate that ITX inhibits endosteal bone resorption and mildly increases periosteal bone formation.

On the other hand, the E2 group showed that inhibition of endosteal bone resorption led to inhibition of increase in endosteal circumference and also showed a decrease in periosteal circumference, compared to the OVX group and a 9.8% increase in cortical bone thickness, compared to the OVX group. The effect of E2 on inhibition of decrease in cortical bone thickness is attributed to inhibited bone metabolism turnover. These results conform to existing knowledge.

Bone strength is more important for evaluation of the effectiveness of therapeutic or preventive drug for osteoporosis than bone structure (BMC and BMD) and bone mass (cortical bone thickness and cortical bone periosteal and endosteal circumferences).

In the experiment, three bone strength indexes were measured: PSSI (polar-axis strength index), XSSI (X-axis strength index), and YSSI (Y-axis strength index).

The OVX group showed a 15.1% decrease in PSSI and a 14.7% decrease in XSSI, compared to the Sham group. The ITX50 group showed an increase in the three bone strength indexes, compared to the OVX group: 16.2% increase in PSSI, 24.0% increase in YSSI, and 14.2% increase in XSSI. The effect of ITX on inhibition of decrease in bone strength indexes is thought to be attributed to inhibited decrease in cortical bone thickness, suggesting that ITX has a strong anti-fracture activity. It is well known that the greatest fear among those who have osteoporosis is bone fracture.

The E2 group showed a 15.3% increase in XSSI and a 23.5% increase in YSSI, compared to the OVX group.

Table 4 shows the results of the measurements of body weight of the rats at the beginning and the end of the experiment and the measurements of their uterine weight at the end of the experiment.

These results suggest that there is a different mechanism in action between ITX and E2. It has been known that E2 has an effect on bone and works against uterus and breast, increasing the risk of their cancer. The results suggest also that ITX acts on osteoporosis without increasing the risk of uterine cancer.

INDUSTRIAL APPLICABILITY

Drugs of the present invention may be used for treatment or prevention of osteoporosis.

The invention claimed is:

1. A method of treating osteoporosis, comprising:
    identifying a patient having osteoporosis, and
    administering to the patient a compound shown in formula (1) or a pharmaceutically acceptable salt or ester of said compound shown in formula (1) as an effective ingredient,

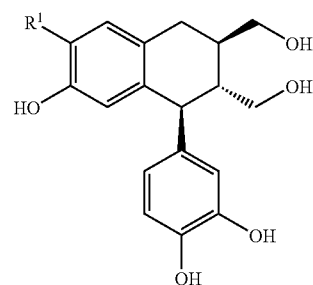

(1)

wherein $R^1$ is an alkyloxy group having a carbon number of 1 to 4.

2. The method of claim 1, wherein $R^1$ is an alkyloxy group having a carbon number of 1 to 2.

3. The method of claim 1, wherein $R^1$ is an alkyloxy group having a carbon number of 1.

4. A method of promoting bone formation in a patient in need of bone formation promotion, comprising:
    identifying the patient in need of bone formation promotion, and

TABLE 4

| Body weight and uterine weight | | | | | |
|---|---|---|---|---|---|
|  | Sham | OVX | E2 | ITX100 | ITX50 |
| Body weight at the beginning (g) | 286 ± 21 | 294 ± 22 | 296 ± 17 | 296 ± 21 | 284 ± 8 |
| Body weight at the end (g) | 306 ± 31 | 333 ± 20# | 299 ± 33** | 301 ± 15* | 318 ± 18 |
| Uterine weight (mg) | 780 ± 79 | 223 ± 45## | 401 ± 81*** | 238 ± 89 | 231 ± 69 |

At the end of the experiment, the OVX group showed a significant increase in body weight (13.4%) and a remarkable decrease in uterine weight (71.4%), compared to the Sham group.

Both the comparison of the difference between the ITX100 group, the ITX50 group and the Sham group and the difference between the OVX group and the Sham group revealed that the ITX100 group and the ITX50 group showed inhibition of increase in body weight at the end of the experiment and showed no significant difference in uterine weight, compared to the OVX group.

On the other hand, the comparison of the difference between the E2 group and the Sham group and the difference between the OVX group and the Sham group revealed that the E2 group showed inhibition of increase in body weight at the end of the experiment and inhibition of decrease in uterine weight (48.5% decrease, compared to the Sham group).

administering to the patient a compound shown in formula (1) or a pharmaceutically acceptable salt or ester of said compound shown in formula (1) as an effective ingredient,

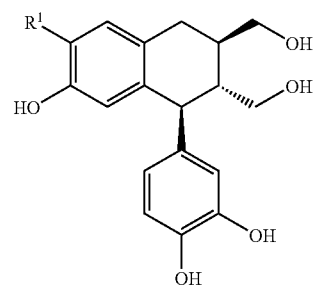

(1)

wherein $R^1$ is an alkyloxy group having a carbon number of 1 to 4.

5. The method of claim 4, wherein $R^1$ is an alkyloxy group having a carbon number of 1 to 2.

6. The method of claim 4, wherein $R^1$ is an alkyloxy group having a carbon number of 1.

* * * * *